(12) United States Patent
Weinstein et al.

(10) Patent No.: US 9,791,395 B2
(45) Date of Patent: Oct. 17, 2017

(54) THERMOGRAPHY-BASED METHOD FOR DETECTING DEFECTS IN SEALS WITH CONDUCTIVE INNER-SEALS

(71) Applicant: D.I.R. TECHNOLOGIES (DETECTION IR) LTD., Haifa (IL)

(72) Inventors: Yoav Weinstein, Atlit (IL); Eran Sinbar, M.P. Misgav (IL)

(73) Assignee: D.I.R. Technologies (Detection IR) Ltd., Haifa, IL (US)

( * ) Notice: Subject to any disclaimer, the term of this patent is extended or adjusted under 35 U.S.C. 154(b) by 0 days.

(21) Appl. No.: 14/888,532

(22) PCT Filed: May 1, 2014

(86) PCT No.: PCT/IL2014/050396
§ 371 (c)(1),
(2) Date: Nov. 2, 2015

(87) PCT Pub. No.: WO2014/178056
PCT Pub. Date: Nov. 6, 2014

(65) Prior Publication Data
US 2016/0054245 A1     Feb. 25, 2016

(30) Foreign Application Priority Data

May 2, 2013   (IL) .......................... 226111

(51) Int. Cl.
*G01N 25/72*    (2006.01)
*B29C 65/82*    (2006.01)
(Continued)

(52) U.S. Cl.
CPC ........... *G01N 25/72* (2013.01); *B29C 65/368* (2013.01); *B29C 65/3656* (2013.01);
(Continued)

(58) Field of Classification Search
CPC ...................................................... G01N 25/72
See application file for complete search history.

(56) References Cited

U.S. PATENT DOCUMENTS

| | | | |
|---|---|---|---|
| 7,434,986 B2 | 10/2008 | Ignatowicz | |
| 2006/0039444 A1* | 2/2006 | Brun ................... | B29C 65/3656 374/45 |

(Continued)

FOREIGN PATENT DOCUMENTS

| | | |
|---|---|---|
| CA | 1 145-711 | 2/1981 |
| EP | 0 355 699 | 2/1990 |

(Continued)

OTHER PUBLICATIONS

"Super Seal™ extends shelf life and seals Jus-Made's diverse product mix"; *New Cap sealing technology*; Oct. 5, 2007, XP055125438, retrieved from the Internet; http://www.enercoind.com/mediaLib/csml/newsletters/cs07q4.pdf; retrieved on Jun. 26, 2014.

(Continued)

*Primary Examiner* — David Porta
*Assistant Examiner* — Hugh H Maupin
(74) *Attorney, Agent, or Firm* — Haug Partners LLP; William S. Frommer

(57) ABSTRACT

The present disclosure provides a method for detecting thermal sealing defects of a container during its transportation along a process line. The method is particularly suitable for containers caped with a cap liner and sealed with an inner seal. The method makes use of a high frequency heat (e.g. by a high frequency heat induction unit) to cause eddy current in the inner seal after which there is sensing by an IR imager of radiation emitted from the conductive innerseal to generate sensed IR image data indicative of the sensed radiation. The sensing is characterized by at least one of (i) a time window of a sensing session of between 50 msec to (Continued)

300 msec during which said container is being transported through the FOV; and (ii) a sensing range of a wavelength spectrum region from 2 μm to 6 μm. The IR data is then processed so as to generate output data indicative of the presence or absence of at least one defect in the sealing of the container by said innerseal.

20 Claims, 5 Drawing Sheets

(51) Int. Cl.
| | |
|---|---|
| *B29C 65/36* | (2006.01) |
| *B29C 65/00* | (2006.01) |
| *G01N 21/3563* | (2014.01) |
| *G01N 21/71* | (2006.01) |
| *G01N 33/00* | (2006.01) |
| *B29L 31/00* | (2006.01) |
| *B29L 31/56* | (2006.01) |

(52) U.S. Cl.
CPC ...... *B29C 65/8261* (2013.01); *B29C 65/8284* (2013.01); *B29C 66/112* (2013.01); *B29C 66/114* (2013.01); *B29C 66/53461* (2013.01); *B29C 66/72321* (2013.01); *B29C 66/72328* (2013.01); *G01N 21/3563* (2013.01); *G01N 21/71* (2013.01); *B29L 2031/565* (2013.01); *B29L 2031/7158* (2013.01); *G01N 2033/009* (2013.01)

(56) References Cited

U.S. PATENT DOCUMENTS

| | | | | |
|---|---|---|---|---|
| 2006/0288663 | A1* | 12/2006 | Herzog | 53/478 |
| 2011/0293166 | A1* | 12/2011 | Sinbar et al. | 382/141 |
| 2011/0315881 | A1* | 12/2011 | Knowles | H04N 5/243 250/352 |
| 2012/0279968 | A1 | 11/2012 | Sarraf et al. | |
| 2015/0049182 | A1* | 2/2015 | Scharer | G01N 21/8422 348/91 |

FOREIGN PATENT DOCUMENTS

| | | |
|---|---|---|
| EP | 1 623 930 | 2/2006 |
| EP | 1 882 579 | 1/2008 |
| EP | 2 453 225 | 5/2012 |
| EP | 2 453 225 | 6/2012 |
| JP | 10318955 | 12/1998 |
| JP | 2003 307505 | 10/2003 |
| JP | 2003307505 | 10/2003 |
| JP | 10 318955 | 12/2004 |
| WO | WO 2007/147158 | 12/2007 |
| WO | WO 2013/057731 | 4/2013 |

OTHER PUBLICATIONS

International Search Report mailed Jul. 3, 2014.
"Super Seal Max extends shelf life and seals Jus-Made's diverse product mix," Packaging World Magazine, 4$^{th}$ quarter, 2007, Enercon Industries: www.enerconind.com/sealing.

* cited by examiner

Cooled Detector

Un-cooled Detector

Cooled Detector

Un-cooled Detector

THERMOGRAPHY-BASED METHOD FOR DETECTING DEFECTS IN SEALS WITH CONDUCTIVE INNER-SEALS

This is a 371 of application serial number PCT/IL2014/050396, filed May 1, 2014, which is entitled to the priority filing date of Israel application 226111, filed on May 2, 2013, the entirety of which is incorporated herein by reference.

TECHNOLOGICAL FIELD

The present disclosure concerns a method for detection of defects in thermal sealing of containers.

PRIOR ART

References considered to be relevant as background to the presently disclosed subject matter are listed below:
- Japanese unexamined patent application publication No. 2003-307505.
- U.S. Pat. No. 7,434,986.
- International Patent Application Publication No. WO2007/147158.
- European Patent Application Publication No. EP0355699.

Acknowledgement of the above references herein is not to be inferred as meaning that these are in any way relevant to the patentability of the presently disclosed subject matter.

BACKGROUND

Induction sealing, otherwise known as cap sealing, is a non-contact method of heating a metallic disk to hermetically seal the top of plastic and glass containers. This sealing process takes place after the container has been filled and capped.

The closure is supplied to the bottler with aluminum foil liner already inserted. A typical induction liner is multi-layered. The top layer (distanced from the container opening) is a paperpulp that is generally spot-glued to the cap. The next layer is wax that is used to bond a layer of aluminum foil to the pulp. The bottom layer is a polymer film laminated to the foil. In conventional capping techniques, after the cap is applied over the opening of the container, the container passes under an induction coil, which emits an oscillating electromagnetic field and the conductive aluminum foil liner begins heats. The heat melts the wax, which is absorbed into the pulp backing and releases the foil from the cap. The polymer film also heats and flows onto the lip of the container. When cooled, the polymer creates a bond with the container resulting in a hermetically sealed product. Neither the container nor its contents are affected, and this all happens in a matter of seconds or even less.

At times, it is possible to overheat the foil causing damage to the seal layer and to any protective barriers. This could result in faulty seals, even weeks after the initial sealing process.

Japanese unexamined patent application publication No. 2003-307505 describes a thermography based system for detecting defects in the fusion of the aluminum seal to a bottle's opening.

In addition, U.S. Pat. No. 7,434,986 describes an apparatus for monitoring and detecting sealing defects. The system described in U.S. Pat. No. 7,434,986 includes a thermal imager that is mounted along a process line that transports an object having at least one recently created thermal seal.

Yet, in addition, PCT publication WO2007/147158 describes a pulsed thermography defect detection apparatus including active and passive infrared (IR) thermography for non-destructive testing (NDT) of powdermetallic (P/M) components for on-line and off-line inspection.

Yet, further, European patent application publication EP0355699 describes a method for inspecting leakage of a sealed container, the method being based on changing an internal pressure of a vacuum chamber and having a conductive material at least at a portion to be inspected in the chamber and determining any change in the amount of expansion after a time when the detected amount of expansion shows the maximum value, to thereby to find out defects in the sealed container.

GENERAL DESCRIPTION

The present invention provides a method for detecting thermal sealing defects of a container during its transportation along a process line, the method comprises:
inducing high frequency heat onto a container (e.g. by transferring the container through a high frequency heat induction (HFHI) unit) comprising a base and side walls defining a void that holds a product, the container further comprising an opening at a top end of the side walls, the opening being sealed with a conductive innerseal or having superimposed thereon a conductive innerseal, and being further enclosed over the innerseal by a container cap equipped with a compressible cap liner facing the innerseal, the induction causing eddy current in said conductive innerseal;
transporting the container into a field of view (FOV) of an IR imager positioned along said process line being above said container cap;
sensing by said IR imager radiation emitted from said conductive innerseal and generating sensed IR image data indicative of the sensed radiation, wherein said sensing is characterized by at least
  a time window of a sensing session of between 50 msec to 300 msec during which said container is being transported through the FOV; and
  a sensing range of a wavelength spectrum region from 2.0 µm to 6 µm,
processing said IR image data and generating output data indicative of the presence or absence of at least one defect in the sealing by said innerseal.

Also provided by the present invention is a program storage device readable by machine tangibly embodying a program of instructions executable by the machine to perform a method for detecting thermal sealing defects of a container during its transportation along a process line, the method being as defined above.

Also provided by the present invention is a computer program product comprising a computer useable medium having computer readable program code embodied therein for detecting thermal sealing defects of a container during its transportation along a process line, the computer program product comprising:
(a) computer readable program code for causing the induction of high frequency heat onto a container comprising a base and side walls defining an inner void that holds a product, the container further comprising an opening at a top end of the side walls of said container, the opening being sealed with a conductive innerseal or having superimposed thereon a conductive innerseal, and further being enclosed over the conductive innerseal with a container cap equipped with a compressible cap liner facing the innerseal, said induction causes eddy current in said conductive innerseal;

(b) computer readable program code for causing transportation of the container into a field of view (FOV) of an IR imager positioned along said process line and above said container cap;

(c) computer readable program code for causing sensing by said IR imager radiation emitted from said conductive innerseal and generating sensed IR image data indicative of the sensed radiation, wherein said sensing is characterized by at least
a time window of a sensing session of between 50 msec to 300 msec during which said container is being transported through the FOV; and
a sensing range of a wavelength spectrum region from 2.0 μm to 6.0 μm, (d) computer readable program code for causing the computer to process said IR image data and generating output data indicative of the presence or absence of at least one defect in the sealing by said innerseal.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
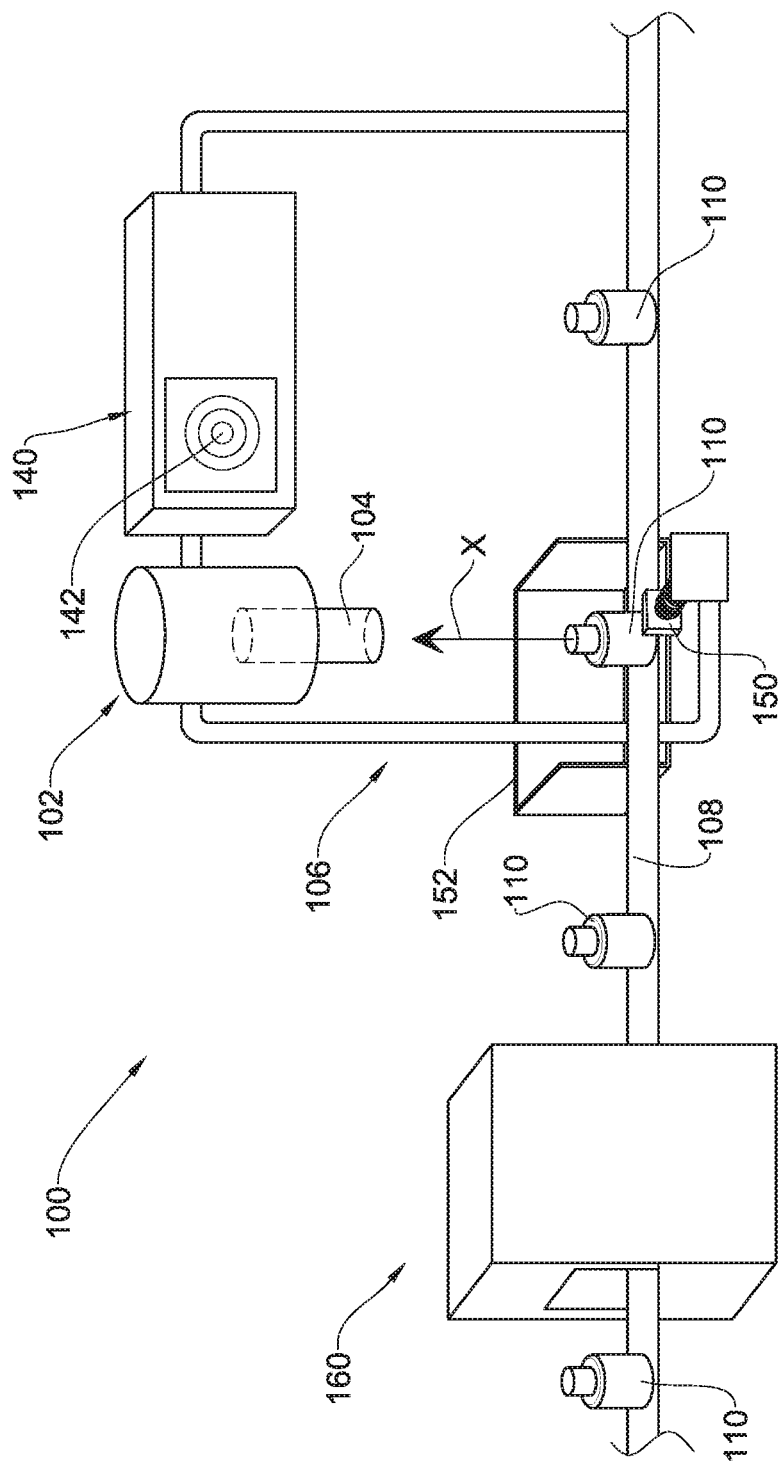
FIG. 1 is a schematic illustration of a system for performing the method according to one embodiment of the present disclosure.

The present invention is based on the understanding that there is a need in the art, in particular, the pharmaceutical arena, to monitor and detect defects in sealing of products during manufacturing processes and On Line determine the fate of a manufactured product, e.g. when the seal is defected, and if necessary, alter the process to improve quality of the sealing for the following, in line, products.

In this respect and for this purpose, the inventors have developed unique conditions and system construction that allow to image the sealing of inner seals of containers, such a the aluminum seals of bottles, that are already enclosed with a cap containing cap liner, the latter being typically non-transparent to IR. In other words, the present disclosure provides a solution for imaging sealing of containers capped with a cap equipped with a cap liner.

As such, in accordance with the present disclosure there is provided a method for detecting thermal sealing defects of a container being transported along a process line, the method comprises:

causing eddy current in a conductive innerseal of a container having an inner volume being defined by a container base and side walls, and holding in the inner volume (void within the side walls) a product, preferably, healthcare product, the container further comprising an opening at a top end of the container's side walls which is sealed with the conductive innerseal or has superimposed thereon a conductive innerseal, the opening further being enclosed (superimposed over the conductive innerseal) with a container cap;

transporting the container through a field of view (FOV) of an IR imager positioned along said process line and above the container cap;

sensing by the IR imager radiation emitted from said conductive innerseal and generating sensed IR image data indicative of the sensed radiation, wherein the sensing is characterized by at least
a time window of a sensing session of between 50 msec to 300 msec during which said container is being transported through the FOV; and
a sensing range of a wavelength spectrum region from 2.0 μm to 6.0 μm, processing said IR image data and generating output data indicative of the presence or absence of at least one defect in the sealing by said conductive innerseal.

One unique feature of the present disclosure reside in the fact that the induction of high frequency heat onto the container has no affect on the product within the container. This is particularly relevant when the product is a healthcare product, such as a pharmaceutical product or a cosmetic product that require complete sealing of the product in order to avoid damage to the product during storage that may occur if the sealing is defected and therefore imaging of the quality of sealing is required without damaging the product per se. In addition, many healthcare products include cap liners (for ensuring firm resealing by the cap container after the innerseal is removed) and/or child resistant mechanisms that form an air void between the cap and the cap liner or innerseal, all of which make is difficult to image the sealing by the innerseal by conventional techniques.

In fact, the present development is targeted and aimed at affecting only the innerseal at its opening (i.e. its top end facing the IR imager, as discussed below). There is no effect or no damage caused to the product within the container or even to the side walls of the container, as these are not in position to be fully imaged by the IR imager.

For better understanding the present development, reference is made to system 100 schematically illustrated in FIG. 1, the system also forming part of the present invention for performing the method disclosed herein in accordance some embodiments.

Specifically, system 100 is configured for detecting thermal sealing defects of a container which is being transported along a process line. To this end, the process line is equipped with a high frequency heat induction (HFHI) unit, such as HFHI unit 160, an infrared (IR) imager 102 comprising a cooled IR detector 104 that is mounted on a holding arm 106. A conveyer belt 108 is configured to transport a container 110 into field of view (FOV) of IR imager 102, the latter being positioned above the location a container 110 when placed on conveyer belt 108. As a result, radiation emitted from container 110 is sensed by IR detector 104 in the direction of arrow X.

Figure 2A:
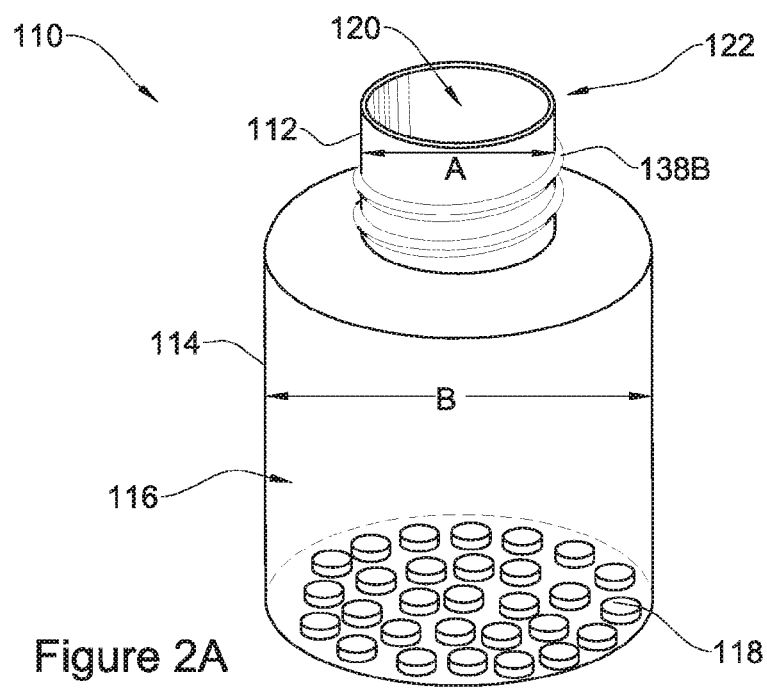
FIGS. 2A-2C are schematic illustrations of a container and a container cap in accordance with an embodiment of the present disclosure.
Figure 2B:
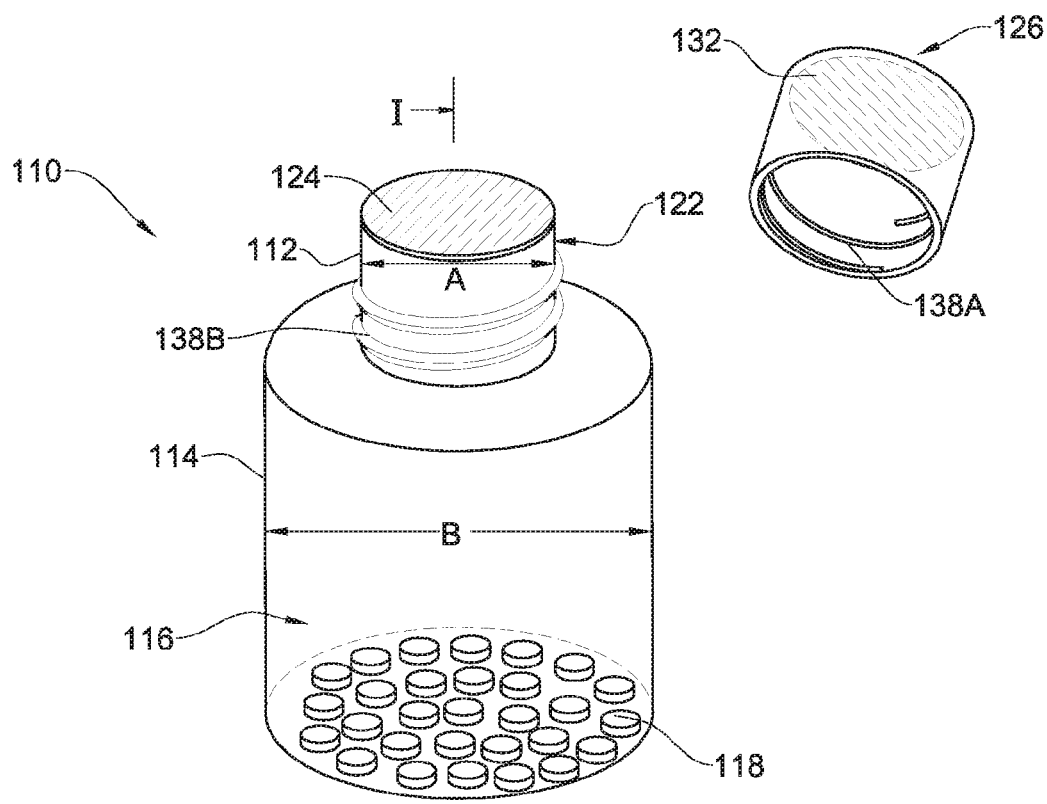

The container 110, is illustrated in an enlarged view in FIGS. 2A and 2B being shown in an open, unsealed configuration, i.e. no container cap over the opening (FIG. 2A) or closed and sealed configuration (FIG. 2B), namely, including a container cap over the container's opened top. In this non-limiting example, container 110 has a neck part 112 defined by a first cross section A, the neck part extending above body part 114 that is defined by a second cross section B. First cross sectional area A is smaller than the second cross sectional area B. Body part 114 provides an inner volume 116 for carrying a product. In this embodiment, the product is a pharmaceutical product illustrated as tablets 118. Neck part 112 ends with a container opening 120 as illustrated in FIG. 2A at container's top end 122.

During a manufacturing process and at the last stage of sealing the product within the container, opening 120 is sealed with a conductive innerseal 124 being illustrated in FIG. 2B, the innerseal 124 may be, without being limited thereto, an aluminum film. In the closed configuration shown in FIG. 2B, innerseal 124 is further enclosed with a container cap 126 superimposed over the innerseal.

Figure 2C:
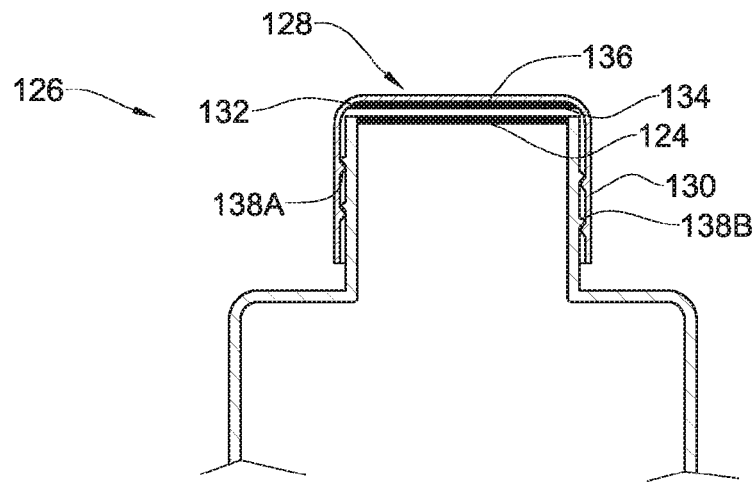

FIG. 2C provides a cross sectional view along line I-I of the container cap illustrated in the enlarged portion of FIG. 2B. Specifically, container cap 126 is defined by a closed end 128 and a rim 130 descending from the closed end 128. Container cap 126 is equipped with a cap liner 132.

As appreciated in various industries and in particular in the pharmaceutical industry the cap liner 132 is essential in order to ensure tight closure of the container once the innerseal, e.g. the aluminum seal over the opening, is removed (i.e. after first opening of the container).

Cap liner 132 may be of any compressible material (to allow pressing the cap onto the opening), and may be, without being limited thereto, a cardboard or a polymeric foam disc. In the context of the present disclosure, when referring to cap liner it is to be understood as optionally also encompassing a child resistance mechanism, known to be used particularly in the pharmaceutical industry. In some embodiments, the cap liner includes both the liner per se, e.g. the cardboard or any similar compressible material (providing the compressibility of the cap towards the container) and the child resistance unit. As appreciated, the child resistance unit is typically in the form of a cap (at time only including the rims of a cap) that is fitted (removably mounted) within the container cap with the rims of the external cap (the container cap) being aligned with the child resistance unit. The inclusion of a child resistant mechanism (e.g. an internal cap) typically forms an air void between the inner surface closed end of the cap (from which the rims descend) and the closed end of the internal child resistance unit. This air-void reduces IR transmittance from the innerseal to the IR imager. Therefore, the present method is particularly of interest in cases of container caps equipped by child resistance mechanism of any other mechanisms that form a layer or air near the cap when the container is capped therewith. As shown, the conditions of the present invention were unique in being able to image through such air gaps.

Cap liner 132 has a first surface 134 and a second surface 136 and is disposed within the closed end 128 of cap 126 such that the cap liner first surface 134 faces the closed end 128 of the cap 126. The cap liner 132 may be removable or permanently adhered to the closed end 128 of the container cap 126, e.g. glued.

Rim 130 has internal threads 138A for enclosing over the container's neck portion 112 via corresponding threads 138B at the outer surface of said neck portion as shown in FIG. 2B.

Turning back to FIG. 1, IR imager 102 is positioned along said process line above conveyer belt 108. In some embodiments, the IR detector 104 is positioned normal to innerseal 124, once container 110 is directly below the IR detector 104. In such embodiments, radiation emitted from the conductive innerseal 124 is sensed by the IR imager 102 or specifically, by the IR detector 104 at least in the direction of arrow X.

In some embodiments, the FOV of IR imager 102 is about between 20 cm×30 cm, at times, 20 cm×25 cm and yet at times, 24 cm×29 cm, and the IR imager 102 is situated between about 40-70, preferably about 60 cm above the conveyer belt 108.

Once the container 110 is within the field of view (FOV) of IR imager 102, the latter senses radiation emitted from container 110 to generated sensed IR image data indicative of the sensed radiation from the container's innerseal 124 (not shown in FIG. 1).

The sensing by the system disclosed herein is characterized by at least one of the following conditions:
  a sensing session of between 50 msec to 300 msec during which the container is being transported through the FOV; and
  a sensing range of a wavelength spectrum region from 2.0 µm to 6.0 µm.

In is to be understood that in the context of the present disclosure, a "sensing session" is defined by a time window during which an individual container is within the FOV of the IR detector. The sensing session may include generating a single IR image of the container, or two or more IR images. In some embodiments, a single IR image is generated and is sufficient to determine quality/lack of defects in the sealing by the innerseal.

Further, in the context of the present disclosure it is to be understood that a "sensing range" is the wavelength spectrum range at which radiation is sensed by the IR detector. There are various cooled IR detectors that may be operated in accordance with the above conditions. The IR detector may either be of a type that senses radiation only at the desired spectral range of 2.0-6.0 µm or may detect radiation at a wider range but uses suitable filters to sense radiation only at this range or in one or more specific wavelengths within this range. At times, the IR detector is one that is configured to sense radiation within the spectral range of 2.8 µm to 5.4 µm. In some other embodiments, the IR detector is one that is configured to sense radiation within the spectral range of 3.0 µm to 5.4 µm. In yet some other embodiments, the IR detector is one that is configured to sense radiation within the spectral range of 3.0 µm to 5.0 µm.

Sensing at a particular wavelength range may be achieved either by using a specific detector, such as a cooled IR detector, or by using filters to filter out undesired wavelengths or wavelength ranges.

In it further noted that in the content of the present disclosure, sensing or detecting defects in the seal cannot be obtained by the use only of IR sensors configured to sense only in the spectral range of 8-14 µm, or 8-12 µm. In other words, there is a need to at least sense radiation in the mid IR range of 2 to 6 µm, preferably in the ranges of 2.8-5.4 µm.

A cooled IR imager, also known as an IR cooled thermal imaging camera has an imaging sensor that is integrated with a cryo-cooler. The cryo-cooler cools down the sensor temperature to cryogenic temperatures. As such, cooled cameras are based on photovoltaic sensors collecting directly the photo-current produced by the scene.

The reduction in sensor temperature provides a reduced thermally-induced noise to a level below that of the signal from the scene being imaged.

In this respect, it is noted that an uncooled IR camera is one in which the imaging sensor does not require cryogenic cooling.

Generally, uncooled IR cameras are based on a microbolometer thermal detector, which consists of an array of pixels, each pixel being a suspended membrane made of a resistive material demonstrating large changes in resistance as a result of minute changes in temperature. In operation, IR radiation with wavelengths between 7.5-14 μm strikes the detector material, heating it, and thus changing its electrical resistance. This resistance change is measured and processed to create an image. Unlike cooled detectors, microbolometers do not require cooling.

The two most commonly used IR radiation detecting materials in microbolometers are amorphous silicon (a:Si) and vanadium oxide (VOx). This type of camera is the most widely used in commercial applications.

In some embodiments, the cooled cameras are based on array of photodiodes made of semiconductor compounds like Indium Antimonide (InSb) or mercury cadmium telluride (HgCdTe), that need to be cooled down to cryogenic temperatures as operating temperature. In some embodiments, the IR detector comprises a cooled sensor. As shown in the following non-limiting examples, some advantages have been obtained when using cooled IR detectors over the uncooled one.

In some embodiments, the IR detector is characterized by a noise equivalent temperature difference (NETD) of not more than 20 mk, at times even not more than 10 mK, which is provided by the use of a cooled IR detector with fast integration time (snapshot mode) which is between few microseconds to several milliseconds (this being different from uncooled detectors with long response time).

It is also noted that cooled cameras are less sensitive to ambient temperature fluctuations because they work with a cryogenically cooled field stop.

In one embodiment, the IR detector is a cooled InSb detector.

According to some embodiments, IR detector is operable to sense said radiation at ambient temperature.

Due to the existence of cap liner it is essential that the IR imager be of a type sensitive enough to sense the heat transmitted from the innerseal to at least the cap liner. Not only that, the IR imager must be of a kind that is capable of providing a clear IR image of the innerseal while the container under investigation is sealed, capped and is conveyed on the conveyer belt, i.e. while in motion.

According to some embodiments, the IR imager is operable to sense radiation caused by inducing eddy current in the innerseal when the innerseal is superimposed over said opening.

In some embodiments, eddy current is induced using a high frequency heat induction (HFHI) unit, such as the unit 160 illustrated in FIG. 1A as part of the process line. HFHI units are well known in the art, and include, without being limited thereto Enercon Superseal 100, Lepel, etc.

According to some embodiments, the IR imager is operable to provide IR image data of at least the innerseal within a time window of between 1 sec to 20 sec from the moment eddy current is induced in the inner seal (e.g. when the container exists the HFHI unit.

Once radiation caused by an HFHI unit is sensed by the IR detector, the IR imager generates one or more IR image data indicative of the sensed radiation in its FOV. The one or more IR image data are then communicated to a processing and control unit.

In some embodiments, a single IR image is generated and is sufficient to provide the required data for determining quality of the sealing and/or where defects in the sealing exist. In such cases, the IR detection may be regarded as one detecting radiation in the spatial domain, i.e. at a single time point.

The processing and control unit that receive the IR image data from the IR imager is configured to determine based on the IR image data the presence or absence of at least one defect in the sealing by said innerseal. It is also configured to present an image of the defect so as to enable identification of the type of defect.

In accordance with the present disclosure a defect in a seal may be of any type known in the art, including a folding of the innerseal, non-adhered regions between the innerseal and cap opening, deformation of the innerseal due to overheating, weak adherence due to underheating.

A determined defect results in the generation of output data indicative of the presence or absence of at least one defect in the sealing by the innerseal. To this end, the processing and control unit may comprise a dedicated output unit, illustrated in this embodiment as a monitor, such as monitor 142 illustrated in FIG. 1A, for visualization of the IR image data and, if necessary, decision making by a user or by the system (algorithmic based) as to the presence or absence of said at least one defect.

The output may also be in the form of a printout (not illustrated) presenting one or more parameters of the innerseal indicative of the presence (or not) of defects in the seal; and/or the output may be in the form of a YES/NO answer (visual or audio) indicating if defects are present (YES), or not (NO). In some embodiments, an algorithm may be used to determine that when an aberration in the imaged innerseal is greater than a predefined threshold then the seal may be considered as containing a defect.

Due to the use of a specifically selected type of an IR image detector, namely, cooled IR detector with a sensing range of between 2-6 μm (or any variations in this range as defined hereinbefore) it is possible to obtain clear images of the sealing, notwithstanding the movement of the container on the conveyer or the existence of cap liner. These parameters are significantly different between cooled IR detectors and uncooled detectors, as depicted in Table 1 below:

TABLE 1

| IR detector differences | | |
|---|---|---|
| Parameter | Cooled (3-5 μm) | Uncooled (8-14 μm) |
| Contrast @ room temp. | 3.6% 1/T | 1.6% 1/T |
| Time constant (exposure time) | 1 msec | 10 msec |
| Calibration (NUC) frequency | Hours | Minutes |
| Sensitivity (typical) | 20 mK | 100 mK |
| Transmission through HDPE | Typically 3 times better at 3-5 | |

It is important to note that the use of a cooled IR sensor, having a calibration frequency (NUC) of hours (as compared to minutes), allows reliably perform process window analysis based on data recorded during the hours between calibration and determine deviations from pre-defined process limits within the process window and if changes in the process are required. Against this, when calibration occurs every several minutes, the deviation from the pre-defined limits may be as a result of a default in the process (than needs to be corrected) but also from the change as a result of calibration.

In some embodiments, the processing and control unit is configured to process two or more sequentially sensed imaged containers, to form historical image data and to determine whether the historical image data meets a threshold. For example, when the historical image data exceeds or is below the predetermined threshold, or a clear undesired trend in relevant production parameters is observed, the processing and control unit may provide a respective signal of same and/or may provide instructions to modify or cause the processing line to modify a process stage along said manufacturing process, based on the historical data. The collection of historical data and processing thereof so as to execute instructions to modify the manufacturing process is at times operated in the form of machine learning driven algorithm.

Image processing may make use of image contrast analysis, edge detection, image arithmetic, cross correlation between images, convolution between images or between an image to a predefined kernel, spatial frequency transformation and/or spatial filtering methods, temporal frequency transformation and temporal filtering methods, Fourier transforms, discrete Fourier transforms, discrete cosine transforms, morphological image processing, finding peaks and valleys (low and high intensity areas), image contours recognition, boundary tracing, line detection, texture analysis, histogram equalization, image deblurring, cluster analysis etc., all as known to those versed in the art of image processing.

In some embodiments the image processing may be performed using MATLAB (The Mathworks, Inc) software. As appreciated, any image or signal processing algorithm known in the art may be equally applied in the context of the present invention. The analysis may be in the spatial domain or time domain or both.

As also illustrated in FIG. 1A, system 100 may also comprise a displacement unit/arm 150 communicably connected to processing and control unit 140 and is configured to displace any pharmaceutical container, for which a defect is sensed by IR imager 102. Upon detection of a defect, processing and control unit 140 activates displacement unit 150 so as to remove the defected container from the conveyer and thus from the process line, e.g. into a collecting unit 152. Displacement unit 150 may be constructed in any suitable form, e.g. in the form of a piston or a lifting arm etc.

Figure 3:
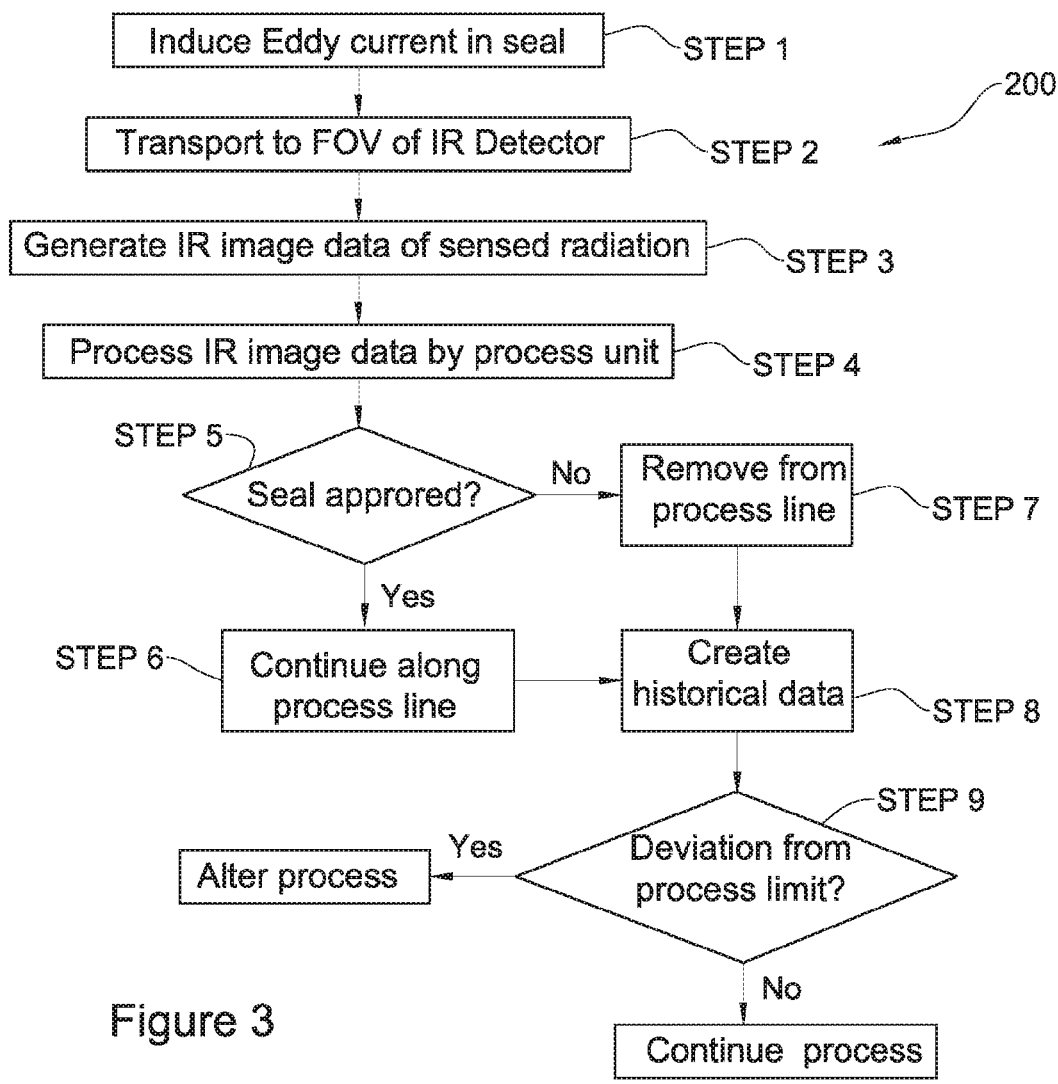
FIG. 3 is a block diagram of the steps for performing the method according to an embodiment of the present disclosure.

The method disclosed herein may be operated as illustrated in a non-limiting block diagram 200 provided in FIG. 3. Specifically, during a manufacturing process line, pharmaceutical containers are placed on and transported in sequence on conveyer belt. The velocity of the conveyer is typically between 200 mm/sec and 600 mm/sec, at times, between 350 and 450 mm/sec and typically about 400 mm/sec.

It is importantly noted that an advantage of using a cooled IR imager is exhibited in industrial process, such as in the pharmaceutical industry, where products are in movement along a process line. Specifically, imaging a product with an uncooled IR imager that typically has an exposure time of 10 msec, and the product being in movement at a velocity of 400 mm/sec will inherently result in the smearing of the image at a range of 4 mm which is a typical size of a defect (e.g. defaulted or incomplete) in the seal of a pharmaceutical container. As such, using uncooled IR images would not be reliable for such processes. Against this, the cooled IR imager, such as those used in the context of the present disclosure, have a much shorter exposure time (about 1 msec) and thus are reliable in imaging objects under movement.

As a first stage in sealing the pharmaceutical container is transported into a high frequency heat induction (HFHI) unit for inducing heat in the container's heat conductive innerseal and causing the sealing (Step 1). The HFHI is operated in accordance the particular manufacturing instructions.

Each heat-induced pharmaceutical container is then continued to be transported on the conveyer belt, into the FOV of the IR imager (Step 2). Once heat sensed by the IR detector of the IR imager, the IR imager generates IR image data indicative of the sensed radiation (Step 3) and the image data is processed by the processing and control unit in order to determine if there is at least one defect in the seal and at times, indicate the type/location of the defect (Step 4). It is essential that during a sensing session, the IR imager is positioned essentially above the container with the plane of the innerseal being perpendicular to an imaginary line from the detector towards the innerseal plane. As noted above, due to the selection of a cooled IR detector with a sensing region of 2-6 µm, the IR image data it is possible to generate a clear IR image of the IR emitted radiation within a short sensing session of between 50 msec to 300 msec. As shown in the following non-limiting examples, use of other types of IR detectors, e.g. un-cooled detectors with a different sensing range generated blurry images that could not be reliable in determining defects in sealing.

Based on the image processing by the processing and control unit a decision is made regarding the sensed container, e.g. Is the seal approved? (Step 5). If processing results in a decision that the sealing of the container is accepted, e.g. within a predetermined threshold (YES answer), the container proceeds into a next process stage according to the manufacturing protocol or is collected for further handling (Step 6). However, if a defect in the seal is determined to exist, i.e. the seal is not within a predetermined threshold and thus not approved (NO answer), the container is displaced from the process line (Step 7).

The processing and control unit is also configured to create data from a series of sequential containers that have been imaged (Step 8). The recorded data, in turn, is compared to a pre-defined process limits and if the recorded data does not fit the process limits, or show a clear trend towards deviation from the pre-defined process limits (Step 9), the processing and control unit may actuate a change in the process line, e.g. to cause calibration of the intensity of the induction power induced in the innerseal.

The present disclosure also provides a program storage device readable by machine, tangibly embodying a program of instructions executable by the machine to perform a method for detecting thermal sealing defects of a container during its transportation along a process line as defined above.

Also provided by the present disclosure is a computer program product comprising a computer useable medium having computer readable program code embodied therein for detecting thermal sealing defects of a container carrying a pharmaceutical product, the container being transportated along a process line, the computer program product comprising:

(a) computer readable program code for causing introduction into a high frequency heat induction (HFHI) unit the container, wherein the container comprises an inner volume carrying a pharmaceutical product and an opening at a top end of side walls of said container, the opening being enclosed with a container cap equipped with a compressible cap liner and the opening further being sealed with a conductive innerseal or having superimposed thereon a conductive innerseal, said introduction into the HFHI unit causes eddy current in said conductive innerseal;

(b) computer readable program code for causing transportation of the container from said HFHI unit into a field of view (FOV) of an IR imager positioned along said process line being above said container;

(c) computer readable program code for causing sensing by said IR imager radiation emitted from said conductive innerseal and generating sensed IR image data indicative of the sensed radiation, wherein said sensing is characterized by at least a time window of a sensing session of between 50 msec to 300 msec during which said container is being transported through the FOV; and a sensing range of a wavelength spectrum region from 2 µm to 6 µm, (d) computer readable program code for causing the computer to process said. IR image data and generating output data indicative of the presence or absence of at least one defect in the sealing by said innerseal.

Description of Some Non-Limiting Examples

The following non-limiting examples are aimed at providing a comparison between seal defect detection using two different types of IR detectors and to establish the superiority of a cooled IR detector operating at the mid wave IR range of 3-5 µm over an un-cooled IR detector operating at the long wave IR range of 8-14 µm.

The comparison was conducted in a system as illustrated in FIG. 1, with the exception that along the process line also an uncooled imager is positioned above the conveyer belt, using the following equipment and conditions:

High frequency heat induction (HFHI) unit: Enercon Super seal induction sealer, LM5022-206 operating at 85% of maximum power Cooled IR camera: Pelican, 640×512 pixels, 15 µm pitch, InSb, cooled detector, operating at MWIR (3-5 µm).

Un-cooled IR camera: Bird 384, 384×288 pixels, 25 µm pitch, VOx, uncooled microbolometer detector, operating at LWIR (8-14 µm).

Containers: High density polyethylene bottles as commercially available in the market.

Container cap and cap liner: High density polyethylene cap equipped with a cardboard cap liner. Two types of caps were examined, with or without child resistant mechanism (child resistant caps).

Innerseal: aluminum foil laminate.

Speed of conveyer belt: 400 mm/sec.

Temperature of environment: room temperature.

Figure 4A:
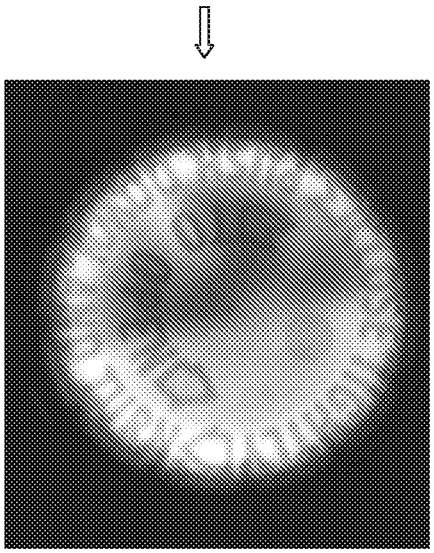
FIG. 4A-4D are images of container caps sensed using cooled IR detector (FIGS. 4A, and 4C) and uncooled IR detector (FIGS. 4B and 4D).
Figure 4B:
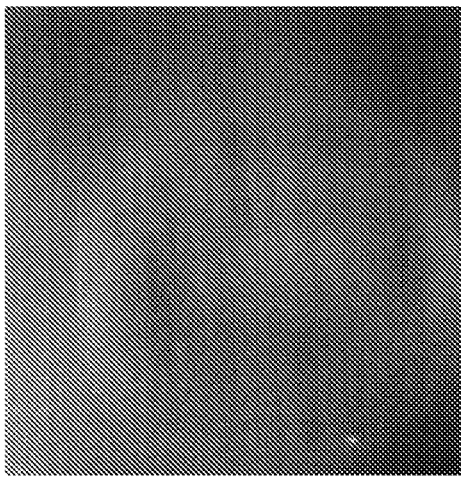
Figure 4C:
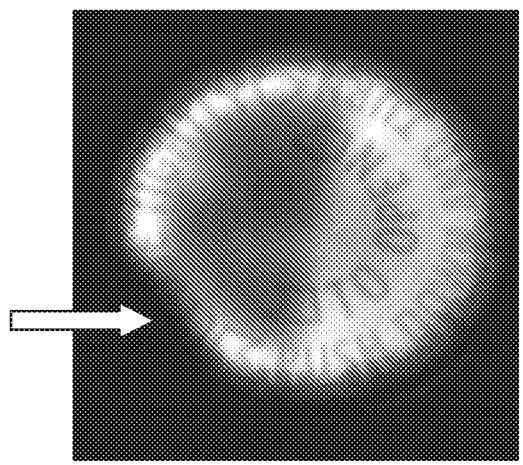
Figure 4D:
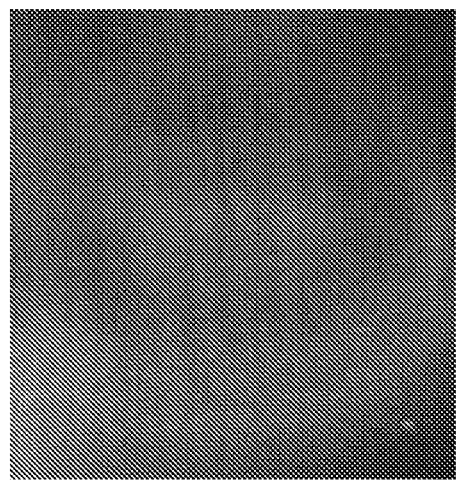

Time of entrance into FOV of cooled or uncooled IR detector after induction and time in FOV of cooled IR detector: 5 seconds after induction and 300 msec in FOV The results are shown in FIGS. 4A-4D with FIGS. 4A and 4C being images generated using the cooled IR detector, and FIGS. 4B and 4D being image generated by the un-cooled IR detector. All images are taken when object is in motion and in all images the cap liner includes a child resistant mechanism (together with the compressible material/liner).

Specifically, FIG. 4A shows a clear image of a complete circle of the conductive aluminum foil disc indicative that the sealing over the opening of the container was complete. In comparison, FIG. 4B, which is the image of the same container generated with the uncooled IR detector, is smeared and blurry and does not provide any information regarding the sealing of the container.

Further, FIG. 4C shows a clear image of a defect zone in the sealing exhibited by as a truncated circle which is a result of a fold in the aluminum foil (see arrow marking the defected zone), this being in comparison to FIG. 4D where the image of the same container generated by the uncooled IR detector is smeared and blurry and does not allow any determination regarding its sealing, which has the same defect in the same zone shown by the arrow in FIG. 4C.

Figure 5A:
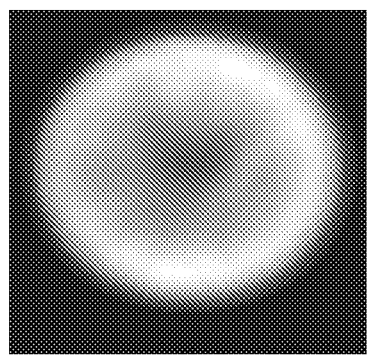
FIG. 5A-5F are images of container caps sensed using cooled IR detector (FIGS. 5A, 5C, 5E) and uncooled IR detector (FIG. 5B, 5D, 5F).
Figure 5B:
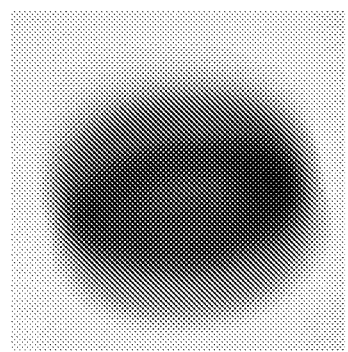
Figure 5C:
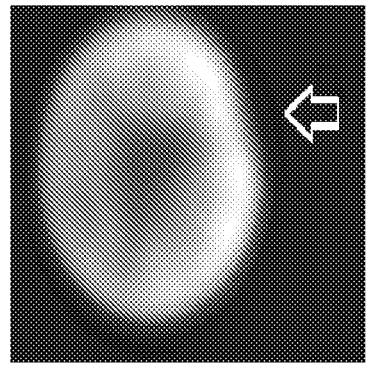
Figure 5D:
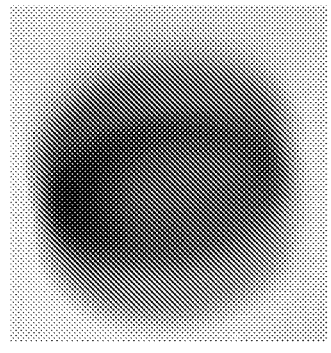
Figure 5E:
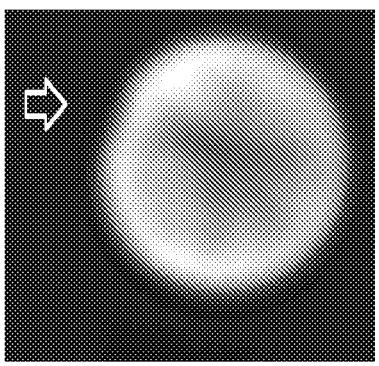
Figure 5F:
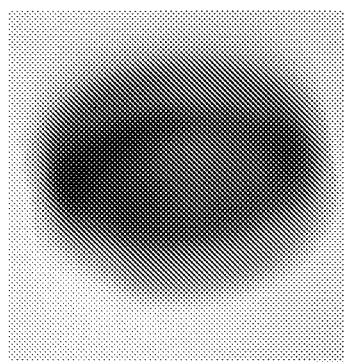

Similarly, FIGS. 5A-5F provide image of intact innerseal (no defects) as shown in FIG. 5A with the cooled IR detector, or images of the same seals, using un-cooled IR detectors (FIG. 5B), or images of defected/folded seals using cooled IR detector, as shown in FIGS. 5C and 5E (arrows indicating the defect caused by a fold in the foil) in comparison with images of the same defected seals, obtained with un-cooled IR detector, as shown, respectively, in FIGS. 5D and 5F. The caps did not include child resistant mechanism.

Clearly, the images show a smearing effect in the images obtained with the uncooled IR detector, which makes it impossible to determine at a reliable level of confidence, particularly, during a manufacturing process, if sealing is defected or not.

The above finding were strengthened when similarly, images of caps with or without a cap liner, and respectively, with or without child resistant mechanism (data not shown) during movement along a process line (velocity of conveyer 400 mm/sec).

The above results provide clear evidence for the superiority of using a cooled IR detector for determining quality of sealing when a cap is equipped with a cap liner and further when there is also child resistant mechanism. This finding is unexpected as the presence of the cap liner constitutes an isolated for the heat to be radiated from the innerseal and it would have been expected that due to the presence of the cap liner, the radiation from the innerseal will not be clearly imaged. Nonetheless, the selection of the particular type of IR detectors, as defined herein, allowed imaging even in the presence of the isolating liner.

Specifically, at a speed of movement along the conveyer of 400 mm/sec and with at least one the following characteristics of each camera, there is provided the superiority of the cooled IR detector over the uncooled one, in terms of sealing defects detection on line in an manufacturing process.

| Parameter | Cooled (3-5 µm) | Uncooled (8-14 µm) |
|---|---|---|
| Contrast @ room temp. | 3.6% 1/T | 1.6% 1/T |
| Time constant (exposure time) | 1 msec | 10 msec |
| Calibration (NUC) frequency | Hours | Minutes |
| Sensitivity (typical) | 20 mK | 100 mK |
| Detector Pixel pitch (PS) | 15 µm | 17 µm |
| Number of pixels on the horizontal axis (No. Pix) | 640 | 384 |
| lens focal length (FL) | 19 mm | 35 mm |
| Distance of camera from bottle cap (D) | 40 cm | 40 cm |
| Transmission through HDPE | 3 times better at 3-5 µm | |

According to the above parameters, the horizontal length of the container plane at the conveyor is L=[(PS)*(No. Pix)/(FL)*(D)]=0.164571 m As such, the container cap occupies about ⅓ of the FOV=0.054857 m.

With the uncooled detector the thermal time constant being 10 msec, the cap moves in the FOV only 0.004 m. As such, the container cap moves about 1/10 of its diameter in 10 msec (which is the thermal time constant of the detector). As a result, the thermal image of the cap is smeared. Against this, the integration time of the cooled detector is about 1 msec, 10 times less than that of the uncooled detector. As a result, the cap moves only 1/100 of its diameter during the period of 1 msec, resulting in less smearing effect.

It was shown by the inventors that, unexpectedly, with the cooled camera it is possible to reduce the integration time to few milliseconds thereby reducing the smearing effect caused by moving objects on a conveyer. This is opposed to the uncooled camera that cannot have its integration time changed as it is continuously integrating IR energy from the object, with a thermal time constant about 10-15 millisecond, and as such resulting in a smearing effect for moving objects.

The technical solution provided by the present disclosure is of particular interest to the pharmaceutical industry where the use of cap liner, with or without the child resistance mechanism is prevalent.

The invention claimed is:

1. A method for detecting thermal sealing defects of a container during its transportation along a process line, the method comprises:
    applying high frequency heat onto a container comprising a base and side walls defining an inner volume that holds a product, the container further comprising an opening at a top end of the side walls, the opening being sealed with a conductive innerseal or having superimposed thereon a conductive innerseal, and further being enclosed over the conductive innerseal with a container cap equipped with a compressible cap liner facing the innerseal, such that an air void exists between the container cap and the cap liner conductive innerseal, said high frequency heat causing eddy current in the conductive innerseal;
    transporting the container into a field of view (FOV) of an IR imager positioned along said process line above the container cap;
    sensing by said IR imager radiation emitted from the conductive innerseal and generating sensed IR image data indicative of the sensed radiation, wherein the sensing is characterized by
    a sensing range of a wavelength spectrum region is from 2 μm to 6 μm, said sensing range selected to permit sensing of the radiation being emitted by the conductive innerseal through the air void between the container cap and the cap liner during the transportation of the container through the FOV of the IR imager, said sensed IR image data thereby comprising at least one image of the conductive innerseal,
    processing said sensed IR image data and generating output data indicative of the presence or absence of at least one defect in the sealing by said innerseal.

2. The method of claim 1, wherein said container cap has a closed end and a rim descending from the closed end, and the cap liner having a first surface and a second surface, is disposed within the closed end of the cap such that the cap liner first surface faces the closed end of the cap.

3. The method claim 1, wherein said cap liner is removeably adhered to an interior surface of the cap.

4. The method claim 1, wherein said cap liner is non-transparent to IR radiation.

5. The method of claim 1, wherein said cap liner is a cardboard liner or comprises compressible polymeric foam.

6. The method of claim 5, wherein said cap is fitted with a removable internal cap between its top end and the compressible cap liner.

7. The method of claim 6, wherein the internal cap is a child resistance unit being disposed between the container cap and the cap liner.

8. The method of claim 1, wherein said sensing by said IR imager is performed within a time window of a sensing session of between 50 msec to 300 msec during which said container is being transported through the FOV.

9. The method of claim 1, further comprising sensing heat transmitted from said innerseal to at least the cap liner.

10. The method of claim 9, further comprising sensing heat transmitted to the cap liner and to at least a portion of the cap.

11. The method of claim 1, further comprising removing from the process line a container being detected as having a defect in said seal.

12. The method of claim 1, further comprising operating said IR imager to acquire one or more IR images when said container is in its FOV.

13. The method of claim 12, comprising operating said IR imager to acquire each of the one or more IR images during a time window of not more than 300 msec.

14. The method of claim 1, further comprising transporting the container from a high frequency heat induction (HFHI) unit into the FOV of the IR imager and acquiring at least one IR image within a time window of between 50 msec to 300 msec.

15. The method of claim 1, comprising operating said IR imager by using an IR detector based on a semiconductor material that is selected from the group consisting of Indium antimonide (InSb) and mercury cadmium telluride (HgCdTe, MCT).

16. The method of claim 1, comprising sensing radiation at a spectral range of 2.8-5.4 μm.

17. The method of claim 1, further comprising creating image data from a series of sequential containers to identify a deviation from a pre-defined process limit, and modifying one or more stages in the process line to cause the sealing to be within the process limit.

18. The method of claim 14, comprising sensing radiation at a spectral range of 2.8-5.4 μm.

19. The method of claim 1, comprising operating a cooled IR imager.

20. An automatic inspection system configured for carrying out the method of claim 1 for detecting thermal sealing defects of a container during its transportation on a conveyer along a process line, the system comprising:
    a high frequency heat induction (HFHI) unit configure and operable to create a high frequency heat region to thereby apply predetermined high frequency heat onto a container when in said high frequency region and induce eddy current in a conductive innerseal sealing an opening of the container and being located underneath an interface formed by cap, a cap liner and an air void;
    a cooled IR imager being located downstream of said HFHI unit with respect to a conveying direction, said IR imager having a field of view (FOV) and being configured and operable for detecting radiation of a wavelength spectrum region from 2 μm to 6 μm, to thereby sense radiation emitted by the conductive innerseal and propagating through said interface during passage of said container in said conveying direction through said FOV, and generate sensed IR image data indicative of one or more images of the conductive innerseal; and
    a control unit configured for communication with the IR imager to receive and process said sensed IR image data, and generate output data indicative of the presence or absence of at least one defect in the sealing by said innerseal.

\* \* \* \* \*

UNITED STATES PATENT AND TRADEMARK OFFICE
CERTIFICATE OF CORRECTION

PATENT NO. : 9,791,395 B2  
APPLICATION NO. : 14/888532  
DATED : October 17, 2017  
INVENTOR(S) : Yoav Weinstein et al.

Page 1 of 1

It is certified that error appears in the above-identified patent and that said Letters Patent is hereby corrected as shown below:

In the Claims

In Claim 1, Column 13, Line 33, please change "the cap liner conductive innerseal" to --the cap liner or conductive innerseal--.

In Claim 5, Column 13, Line 64, please change "claim 1" to --claim 4--.

Signed and Sealed this  
Twenty-sixth Day of March, 2019

Andrei Iancu  
*Director of the United States Patent and Trademark Office*